US011622946B2

(12) United States Patent
Ruiz Canovas et al.

(10) Patent No.: US 11,622,946 B2
(45) Date of Patent: Apr. 11, 2023

(54) USES OF A CAROTENOID IN THE TREATMENT OR PREVENTION OF STRESS INDUCED CONDITIONS

(71) Applicant: GREENALTECH, S.L., Barcelona (ES)

(72) Inventors: Eugenia Ruiz Canovas, Granollers (ES); Xavier Álvarez Micó, Tarrasa (ES); Olga Durany Turk, Barcelona (ES); Jordi Segura De Yebra, Barcelona (ES); Jaume Mercadé Roca, El Masnou (ES)

(73) Assignee: GAT THERAPEUTICS, S.L., Barcelona (ES)

( * ) Notice: Subject to any disclaimer, the term of this patent is extended or adjusted under 35 U.S.C. 154(b) by 0 days.

(21) Appl. No.: 16/092,848

(22) PCT Filed: Apr. 11, 2017

(86) PCT No.: PCT/EP2017/058616
§ 371 (c)(1),
(2) Date: Oct. 11, 2018

(87) PCT Pub. No.: WO2017/178456
PCT Pub. Date: Oct. 19, 2017

(65) Prior Publication Data
US 2019/0167607 A1 Jun. 6, 2019

(30) Foreign Application Priority Data

Apr. 11, 2016 (EP) .................................. 16382162

(51) Int. Cl.
| | | |
|---|---|---|
| A61K 31/122 | (2006.01) | |
| A61K 8/31 | (2006.01) | |
| A61K 8/97 | (2017.01) | |
| A61K 31/01 | (2006.01) | |
| A61K 31/047 | (2006.01) | |
| A61K 31/336 | (2006.01) | |
| A23L 33/105 | (2016.01) | |
| A23L 33/15 | (2016.01) | |
| A61K 31/065 | (2006.01) | |
| A23L 33/10 | (2016.01) | |
| A61K 31/05 | (2006.01) | |
| A61Q 19/00 | (2006.01) | |
| A61P 25/28 | (2006.01) | |
| A61P 9/00 | (2006.01) | |
| A61P 25/24 | (2006.01) | |
| A61P 19/10 | (2006.01) | |
| A61P 35/00 | (2006.01) | |
| A61K 31/343 | (2006.01) | |
| A61Q 19/08 | (2006.01) | |
| A61K 36/00 | (2006.01) | |

(52) U.S. Cl.
CPC .......... *A61K 31/122* (2013.01); *A23L 33/10* (2016.08); *A23L 33/105* (2016.08); *A23L 33/15* (2016.08); *A61K 8/31* (2013.01); *A61K 8/97* (2013.01); *A61K 31/01* (2013.01); *A61K 31/047* (2013.01); *A61K 31/05* (2013.01); *A61K 31/065* (2013.01); *A61K 31/336* (2013.01); *A61K 31/343* (2013.01); *A61P 9/00* (2018.01); *A61P 19/10* (2018.01); *A61P 25/24* (2018.01); *A61P 25/28* (2018.01); *A61P 35/00* (2018.01); *A61Q 19/00* (2013.01); *A61Q 19/08* (2013.01); *A23V 2002/00* (2013.01); *A23V 2250/211* (2013.01); *A61K 36/00* (2013.01)

(58) Field of Classification Search
CPC ....................................................... A61K 31/22
See application file for complete search history.

(56) References Cited

U.S. PATENT DOCUMENTS

| | | | |
|---|---|---|---|
| 5,415,869 A | 5/1995 | Straubinger et al. | |
| 5,821,263 A | 10/1998 | Scola et al. | |
| 5,824,701 A | 10/1998 | Greenwald et al. | |
| 5,869,680 A | 2/1999 | Mas et al. | |
| 2004/0248183 A1* | 12/2004 | Argyropoulos ...... | C12Q 1/6883 435/6.16 |
| 2005/0004235 A1* | 1/2005 | Lockwood ............ | C07C 403/24 514/762 |

(Continued)

FOREIGN PATENT DOCUMENTS

| | | |
|---|---|---|
| CN | 1064616 A | 9/1992 |
| CN | 105412062 A | 3/2016 |
| CN | 106334180 A | 1/2017 |

(Continued)

OTHER PUBLICATIONS

PCT International Patent Application Publication No. WO 98/13059, (Bristol-Myers Squibb Company [US]), published Apr. 2, 1998.
PCT International Patent Application Publication No. WO 98/22451 (Soga, T [Jp]); published May 28, 1998 (English Translation).
PCT International Patent Application Publication No. WO 98/28288, (Bristol-Myers Squibb Company [US]), published Jul. 2, 1998.
PCT International Patent Application Publication No. WO 98/58927, (Baker Norton Pharmaceuticals, Inc. [US]), published Dec. 30, 1998.

(Continued)

*Primary Examiner* — Yong S. Chong
(74) *Attorney, Agent, or Firm* — Gary J. Gershik

(57) ABSTRACT

The invention relates to a carotenoid for use in the treatment or prevention of stress induced conditions, and in particular it relates to the treatment or prevention of a disease mediated by glucocorticoid receptor activity. The invention also relates to a cosmetic method for preventing premature-aging of skin in a subject which comprises administering a carotenoid to said subject. Finally, the invention relates to a method for modulating the activity of a glucocorticoid receptor comprising contacting the receptor with a carotenoid.

5 Claims, 8 Drawing Sheets

(56) References Cited

U.S. PATENT DOCUMENTS

| | | | |
|---|---|---|---|
| 2007/0071841 A1* | 3/2007 | Kappagoda | A61P 3/00 424/766 |
| 2007/0128310 A1 | 6/2007 | Honda et al. | |

FOREIGN PATENT DOCUMENTS

| | | | |
|---|---|---|---|
| EP | 0 770 385 | 5/1997 | |
| WO | WO-02058683 A2 * | 8/2002 | A61K 31/01 |
| WO | WO-2004012758 A1 * | 2/2004 | A61P 3/00 |
| WO | WO-2006016357 A1 * | 2/2006 | A21D 13/062 |
| WO | WO-2006016363 A2 * | 2/2006 | A23D 9/013 |
| WO | WO-2006083780 A2 * | 8/2006 | A61K 31/35 |

OTHER PUBLICATIONS

PCT International Patent Application Publication No. WO 99/09021, (Florida State University [US]), published Feb. 25, .1999.

PCT International Patent Application Publication No. WO 99/14209 (Kabushiki Kaisha Yakult Honsha [JP]), published Mar. 25, 1999.

PCT International Patent Application Publication No. WO 99/18113 (Bio Research Corporation of Yokohama [JP]), published Apr. 15, 1999 (including English Translation).

PCT International Patent Application Publication No. WO 02/076390, (Corcept Therapeutics Inc. [US]), published Oct. 3, 2002.

PCT International Patent Application Publication No. WO 02/058683, (Lycored Natural Products Industries Ltd. [IL]), published Aug. 1, 2002.

PCT International Patent Application Publication No. WO 04/069186, (Zeavision LLC [US]), published Aug. 19, 2004.

PCT International Patent Application Publication No. WO 16/139605, (Omniactive Health Technologies Limited [IN]), published Sep. 9, 2016.

PCT International Patent Application Publication No. WO 16/164744, (Kemin Industries, Inc. [US]), published Oct. 13, 2016.

PCT International Patent Application Publication No. WO 16/185232, (Maliaga, Tatiana [GR]), published Nov. 24, 2016.

Almeida et al., "Cytotoxic Activity of Fucoxanthin, Alone and in Combination with the Cancer Drugs Imatinib and Doxorubicin, in CML Cell Lines", Environmental Toxicology and Pharmacology 59, 2017, pp. 1-26.

Asai, A. et al., "Biotransformation of Fucoxanthinol into Amarouciaxanthin a in Mice and HepG2 Cells: Formation and Cytotoxicity of Fucoxanthin Metabolites", Drug Metabolism and Disposition, vol. 32, No. 2, pp. 205-211.

Bechelli, J. et al., "Cytotoxicity of Algae Extracts on Normal and Malignant Cells", Leukemia Research and Treatment, vol. 2011, 2011, pp. 1-7.

Chen, F. et al., "Carotenoid Intake and Risk of Non-Hodgkin Lymphoma: a Systematic Review and Dose-Response Meta-Analysis of Observational Studies", Ann Hematol, 2016.

Choi, E. et al., "Glucocorticoid blockade reverses psychological stress-induced abnormalities in epidermal structure and function", Am. J. Physiol. Regul. Integr. Comp. Physiol., 2006, vol. 291, pp. R1657-R1662.

Czeczuga-Semeniuk, E. et al., "The vitamin A family can significantly decrease the expression of ERβ or ERs positive breast cancer cells in the presence or absence of ER ligands and paclitaxel", Gynecological Endocrinology, 2009, vol. 25, No. 5, pp. 287-293.

Dunn, J.H. and Koo, J., "Psychological Stress and skin aging: a review of possible mechanisms and potential therapies", Dermatology Online Journal, 2013, vol. 19, No. 6, pp. 1-18.

Eid, S. Y. et al., "carotenoids reverse multidrug resistance in cancer cells by interfering with ABC-transporters", Phytomedicine, 2012, vol. 19, No. 11, pp. 977-987.

Flint, M.S. et al., "Induction of DNA damage, alteration of DNA repair and transcriptional activation by stress hormones", Psychoneuroendocrinology, 2007, vol. 32, pp. 470-479.

Flint, M.S. et al., "Chronic exposure to stress hormones promotes transformation and tumorigenicity of 3T3 mouse fibroblasts", Stress, 2013, vol. 16, No. 1, pp. 114-121.

Ganesan, P. et al., "Siphonaxanthin, a marine carotenoid from green algae, effectively induces apoptosis in human leukemia (HL-60) Cells", Biochimica et Biophysica Acta, 2011, vol. 1810, pp. 497-503.

Girao, P. M. et al., "Dietary lycopene supplementation on Nile Tilapia (Oreochromis niloticus) juveniles submitted to confinement: effects on cortisol level and antioxidant response", Aquaculture Research, 2012, vol. 43, pp. 789-798.

Hashimoto, T. et al., "The distribution and accumulation of fucoxanthin and its metabolites after oral administration in mice", British Journal of Nutrition, 2009, vol. 102, pp. 242-248.

Hashimoto, T. et al., "Pharmacokinetics of fucoxanthinol in human plasma after the oral administration of kombu extract", British Journal of Nutrition, 2012, vol. 107, No. 11, pp. 1566-1569.

He, Y. et al., "Expression Profiling of Human Keratinocyte Response to Ultraviolet A: Implications in Apoptosis", J Invest Dermatol, 2004, vol. 122, pp. 533-543.

Hennefent, K.L. and Govindan, R., "Novel formulations of taxanes: a review. Old wine in a new bottle?", Annals of Oncology, 2006, vol. 17, pp. 735-742.

Hertzberg, S. et al., "Animal Carotenoids. 32*. Carotenoids of Mytilus edulis (Edible Mussel)", Acta Chemica Scandinavica, 1988, vol. B 42, pp. 495-503.

Hosokawa, M. et al., "Apoptosis-Inducing Effect of Fucoxanthin on Human Leukemia Cell Line HL-60", Food Sci. Technol. Res., 1999, vol. 5, No. 3, pp. 243-246.

Ishikawa S. et al., "Aniadult T-cell leukemia effects of brown algae fucoxanthin and its deacetylated product, fucoxanthinol", Int. J. Cancer, 2 0 0 8 , vol. 123, pp. 2702-2712.

Kim, K. et al. , "Fucoxanthin induces apoptosis in human leukemia HL-60 cells through a ROS-mediated Bcl-xL pathway", Toxicology in Vitro, 2010, vol. 24, pp. 1648-1654.

Konishi, I. et al., "Halocynthiaxanthin and fucoxanthinol isolated from Halocynthia roretzi induce apoptosis in human leukemia, breast and colon cancer cells", Comparative Biochemistry and Physiology Part C, 2006, vol. 142, pp. 53-59.

Kotake-Nara, E. et al., "Characterization of Apoptosis Induced by Fucoxanthin in Human Promyelocytic Leukemia Cells", Biosci., Biotechnol. Biochem., 2005, vol. 69, No. 1, pp. 224-227.

Krylov, I. et al., "Gastroprotective effect of lycopene in acute gastritis induced by hydrocortisone", Eksperimnetal'naia I klinicheskaia farmakologiia, 2002, vol. 65, No. 3, pp. 19-21.

Maoka, T. et al. , "New $C_{37}$ Skeletal Carotenoid from the Clam, Paphia amabillis", J. Agricu. Food Chem., 2008, vol. 56, pp. 12069-12072.

Matsuno, T. et al., "Carotenoids of Tunicates, III. The Structural Elucidation of Two New Marine Carotenoids, Amarouciaxanthin A and $B^{1.2}$", Journal of Natural Products, 1985, vol. 48, No. 4, pp. 606-613.

Mohammed, M.M. et al., "The cyanobacterium Oscillatoria brevis β-carotene extract modulates alterations of biochemical and hematological circadian patterns in stress-induced rat", Biological Rhythm Research, 2016, vol. 47, No. 3, pp. 339-352.

Mok, I. et al., "Fucoxanthin bioavailability from fucoxanthin-fortified milk: In-vivo and in-vitro study", Food Chemistry, 2018, pp. 79-86.

Potapova, A.A. et al., "Beta-carotene in treatment of adjuvant arthritis and hydrocortisone-induced immunodepression", The $9^{th}$ International Congress of Immunology, 1995, pp. 642.

Sangeetha, R.K. et al., "Bioavailability and metabolism of fucoxanthin in rats: structural characterization of metabolites by LC-MS (APCI)", Mol and Cell Biochem, 2010, vol. 333, pp. 299-310.

Smith, J. et al., "Selective Carotenoid Growth Inhibition in Breast Cancer: Independence of Hormonal Sensitivity", The FASEB Journal, 2015, vol. 29, No. 1, Suppl. 32.3, pp. 1-2.

Stojadinovic, O. et al., "Novel Genomic Effects of Glucocorticoids in Epidermal Keratinocytes", Journal of Biological Chemistry, 2007, vol. 282, No. 6, pp. 4021-4034.

Symonds, R.C. et al . , "Carotenoids in the sea urchin Paracentrotus lividus: Occurrence of 9'-cis-echinenone as the dominant carotenoid

(56) References Cited

OTHER PUBLICATIONS in gonad colour determination", Comparative Biochemistry and Physiology, Part B, 2007, vol. 148, pp. 432-444.
Yamano, Y. et al., "Stereocontrolled First Total Syntheses of Amarouciaxanthin A and B.", Organic Letters, 2013, vol. 15, No. 20, pp. 5310-5313.
Yim, M. et al., "Suppressive Effects of Amarouciaxanthin A on 3T3-L1 Adipocyte Differentiation through Down-regulation of PPARγ and C/EBPα mRNA Expression", Journal of Agricultural and Food Chemistry, 2011, vol. 59., pp. 1646-1652.
Yonekura, L. et al., "Keto-Carotenoids Are the Major Metabolites of Dietary Lutein and Fucoxanthin in Mouse Tissues[1-3]", The Journal of Nutrition, 2010, vol. 140, pp. 1824-1831.
Zhang, X. et al., "carotenoids inhibit proliferation and regulate expression of peroxisome proliferators-activated receptor gamma (PPARγ) in K562 cancer cells", Archives of Biochemistry and Biophysics, 2011, vol. 512, pp. 96-106.
International Search Report issued by the International Searching Authority (ISA/O.E.P.M.) dated Jun. 30, 2017 in connection with International Application No. PCT/EP2017/058616.
Bose et al., "Hepatic Glucocorticoid Receptor Plays a Greater Role Than Adipose GR in Metabolic Syndrome Despite Renal Compensation", Dec. 2016, Endocrinology 157 (12) :4943-4960.
Chrousos, George P. and Tomoshige, Kino, "Glucocorticoid Signaling in the Cell: Expanding Clinical Implications to Compex Human Behavioral and Somatic Disorders", Oct. 2009, Ann N Y Acad Sci 1179:153-166.

Fleseriu et al., "Mifepristone, a Glucocorticoid Receptor Antagonist, Produces Clinical and Metabolic Benefits in Patients with Cushing's Syndrome", Jun. 2012, J Clin Endocrinol Metab 97 (6) :2039-2049.
Gross et al., "Mifepristone Reduces Weight Gain and Improves Metabolic Abnormalities Associated With Risperidone Treatment in Normal Men", Mar. 25, 2010, Obesity 18 (12) :2295-2300.
Huang, Paul L., "A comprehensive definition for metabolic syndrome", 2009, Disease Models and Mechanisms, 2:231-237.
Morton, Michael M., "Obesity and corticosteroids: 11β-Hydroxysteroid type 1 as a cause and therapeutic target in metabolic disease", Mar. 25, 2010, Molecular and Cellular Endocrinology 316:154-164.
Roland, Rosmond, "Role of stress in the pathogenesis of the metabolic syndrome", Jan. 30, 2005, Psychoneuroendocrinology 30:1-10.
Silverman, Marni N., and Sternberg, Esther M., "Glucocorticoid regulation of inflammation and its behavioral and metabolic correlates: from HPA axis to glucocorticoid receptor dysfunction", Jul. 2012, Ann N Y Acad Sci 1261:55-63.
Torrecilla et al., "Liver Upregulation of Genes Involved in Cortisol Production and Action Is Associated with Metabolic Syndrome in Morbidly Obese Patients", Mar. 22, 2012, Obes Surg 22:478-486.
Walker, B.R., "Cortisol—cause and cure for metabolic syndrome?", Dec. 23, 2006, Diabet Med 23 (12) :1281-1288.
Wang, M., "The role of glucocorticoid action in the pathophysiology of the Metabolic Syndrome", Feb. 2, 2005, Nutrition and Metabolism 2 (3) :1-14.

* cited by examiner

USES OF A CAROTENOID IN THE TREATMENT OR PREVENTION OF STRESS INDUCED CONDITIONS

RELATED APPLICATIONS

This application is a § 371 national stage of PCT International Application No. PCT/EP2017/058616, filed Apr. 11, 2017, claiming priority of European Patent Application EP 16 382 162.2, filed Apr. 11, 2016, the contents of each of which are hereby incorporated by reference into this application.

FIELD OF THE INVENTION

The invention relates to the field of the treatment or prevention of stress induced conditions, and in particular it relates to diseases mediated by glucocorticoid receptor activity.

BACKGROUND ART

Stress and other similar pathologic conditions may cause disorders in both the hypothalamic-pituitary-adrenal (HPA) axis and the sympathetic-adrenal-medullary (SAM) axis, which affect the production of glucocorticoids and catecholamines, respectively. These disorders are associated with mild to severe health effects.

Under stress conditions or in other pathologies, such as Cushing's syndrome or diseases of the Adrenal Gland, cortisol is significantly upregulated. This upregulation of cortisol can have a major impact on the immune system, mainly by the suppression of response to infection or injury and it has been linked to osteoporosis, hyperglycaemia, muscle wasting, raised intracranial pressure, wound healing impairment and diurnal rhythm alterations. Links between cortisol upregulation and cognitive disorders, such as depression or psychosis, have also been reported. Cortisol has been used as a marker for cancer survival. Psoriasis, acne and atopic dermatitis, among other skin diseases, are caused or exacerbated by cortisol production. This hormone is also the basis for the development of a broad array of gastrointestinal disorders including inflammatory bowel disease, irritable bowel syndrome, food antigen-related adverse responses, peptic ulcer, and gastroesophageal reflux disease.

At present, upregulation resulting in an excess in endogenous glucocorticoids is mainly treated with drugs that inhibit their biosynthetic pathways or by surgical removal of the suprarenal gland. However, said drugs have multiple adverse side effects and surgical methods are not always a viable option.

Among said drugs, aminoglutethimide inhibits the initial step in the synthesis route starting from cholesterol. Trilostane blocks an earlier enzyme in the same pathway. Both drugs inhibit glucocorticoid synthesis, as well as other adrenal steroids (mineralocorticoids and sex hormones). While aminoglutethimide is no longer used in treatment, trilostane is used in veterinary applications for the treatment of Cushing's syndrome and primary hyperaldosteronism. Metyrapone prevents the formation of hydrocortisone and corticosterone, thus only blocking glucocorticoid synthesis. It is used in the treatment of adrenal tumors, ectopic ACTH (Adrenocorticotropic hormone, also known as corticotropin) production and Cushing's disease. Its adverse effects include the development of hypocortisolism or a compensatory increase in ACTH production resulting from a decrease in cortisol-mediated negative feedback on the corticotropic adenoma. It also causes hirsutism, acne and mineralocorticoid effects (hypertension, hypokalemia and edema). Mitotane has the same effect as metyrapone and is also an adrenolytic agent used primarily to treat adrenal carcinoma. It has serious gastrointestinal, neurological and hepatic side effects and it can induce adrenal insufficiency, hypercholesterolemia and alterations in hormone-binding globulins. The anesthetic drug etomidate inhibits various enzymes in the synthetic pathway. It has a rapid onset of action and given its sedative effects, it is mainly used for acute control of hypercortisolemia in patients with life threatening complications. Ketoconazole is an antifungal agent that, in higher dosages and in combination with other drugs, reduces adrenal steroid production via inhibition of multiple steroidogenic enzymes. The major side effects of ketoconazole are hepatotoxicity, hypogonadism in men and gastrointestinal complaints.

Mifepristone is an alternative treatment for cortisol upregulation. It is a potent antagonist of progesterone receptors and glucocorticoid receptors (GR), although its activity as a partial agonist has also been described. It has been used in the treatment of Cushing's syndrome. However, due to its interaction with the progesterone receptors mifepristone causes dysmenorrhea and abnormal vaginal bleeding in women. In fact, mifepristone is used in combination with a prostaglandin for the termination of pregnancy. Other adverse effects include fatigue, nausea, vomiting, diarrhea, headache, edema, hypertension, and hypokalemia and, rarely, adrenal insufficiency and prolonged cardiac QT intervals. Mifepristone is an FDA-approved drug for the treatment of Cushing's syndrome and it is commercialized under the tradename Korlym. Korlym has received also and orphan designation for treatment of ovarian cancer and is under trials for the treatment of triple-negative breast cancer in conjunction with Erbulin.

Thus, there is a need in the art for the provision of effective treatments for stress induced conditions, and in particular for the provision of effective treatments for diseases mediated by glucocorticoid receptor activity.

SUMMARY OF THE INVENTION

The inventors have identified that carotenoids act as antagonists of the glucocorticoid receptor.

Therefore, in a first aspect, the invention relates to a carotenoid for use in the treatment or prevention of a disease mediated by glucocorticoid receptor activity.

In a second aspect, the invention also relates to a cosmetic method for preventing premature-aging of skin in a subject which comprises administering a carotenoid to said subject.

In a third aspect, the invention relates to a method for modulating an activity of a glucocorticoid receptor comprising contacting the receptor with a carotenoid.

In a fourth aspect, the invention relates to a composition comprising a carotenoid and a taxane.

In a fifth aspect, the invention relates to a composition comprising a carotenoid and a taxane for use in the treatment of cancer.

Finally, in a sixth aspect, the invention relates to a carotenoid for use as an adjuvant in the treatment of cancer with a taxane-containing chemotherapy.

DETAILED DESCRIPTION OF THE INVENTION

A carotenoid for Use in the Treatment or Prevention of a Disease Mediated by Glucocorticoid Receptor Activity In a first aspect, the invention relates to a carotenoid for use in the treatment or prevention of a disease mediated by glucocorticoid receptor activity.

Figure 1:
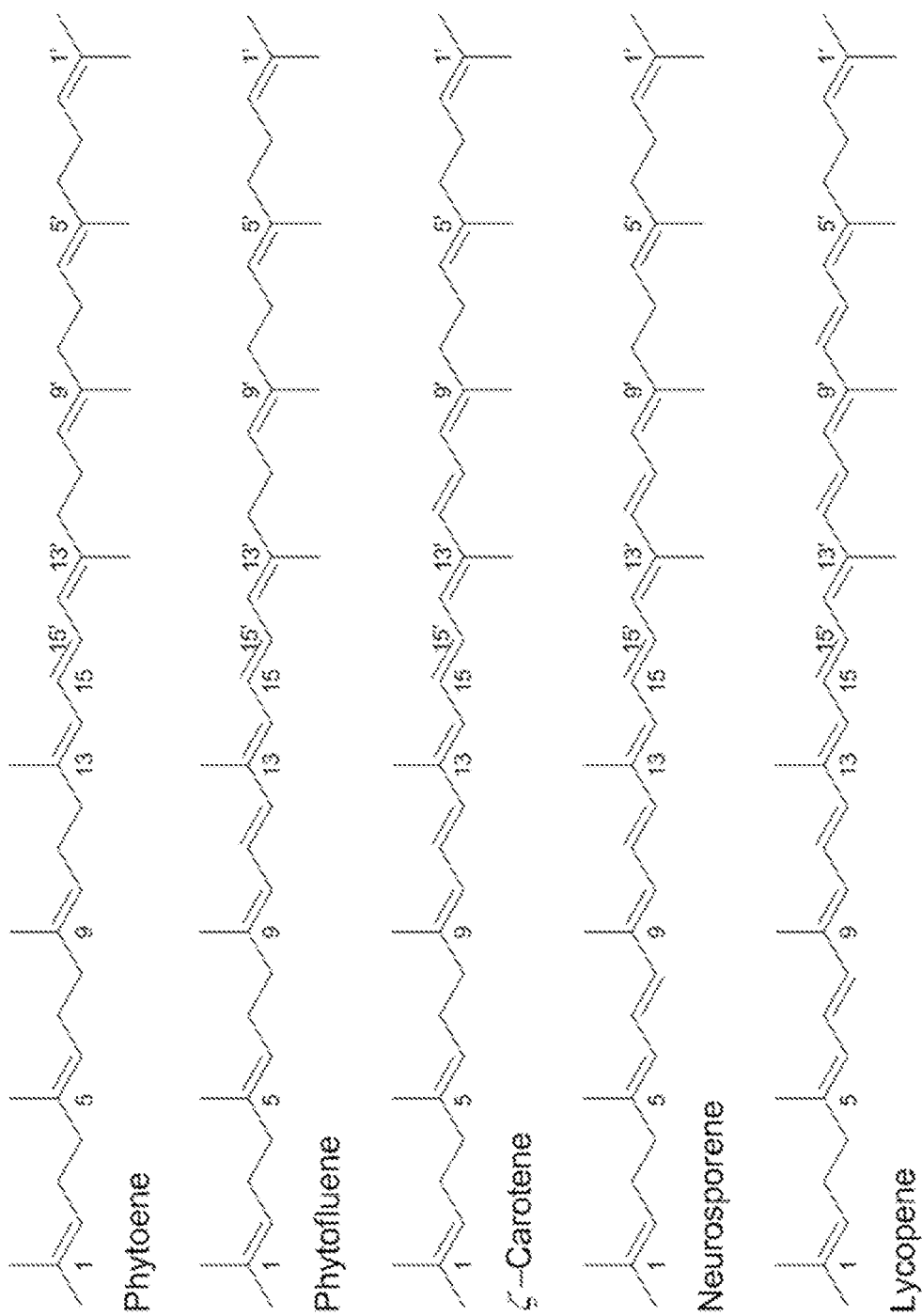
FIG. 1 shows the structure of carotenes phytoene, phytofluene, -carotene, neurosporene, and lycopene.
Figure 2:
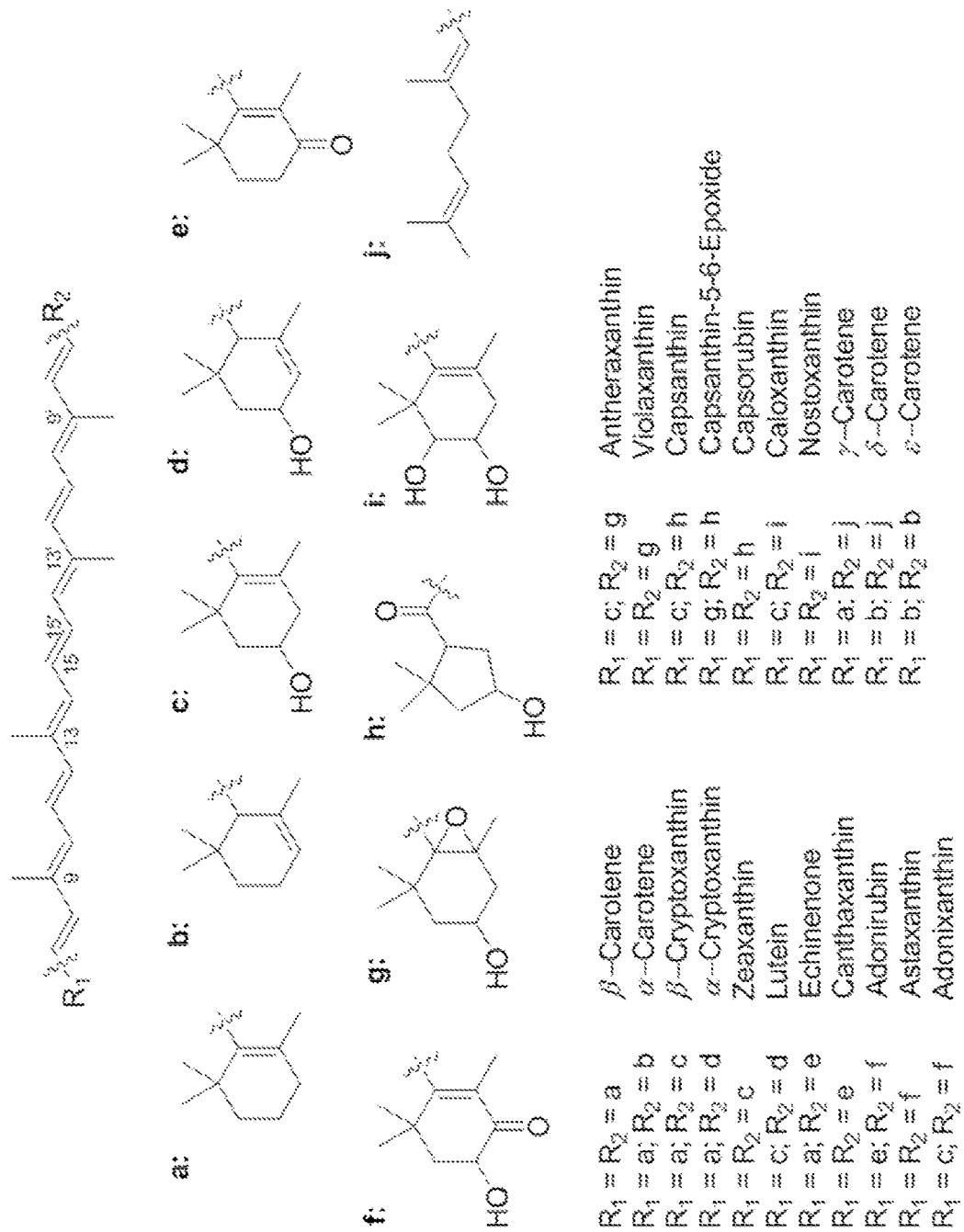
FIG. 2 shows the structure of xantophylls beta-cryptoxanthin, alpha-cryptoxanthin, zeaxanthin, lutein, echinenone, canthaxanthin, adonirubin, astaxanthin, adonixanthin, antheraxanthin, violaxanthin, capsanthin, capsanthin-5-6-epoxide, capsorubin, caloxanthin, and nostroxanthin, and of carotenes α-carotene, β-carotene, γ-carotene, 67-carotene and ε-carotene.
Figure 3:
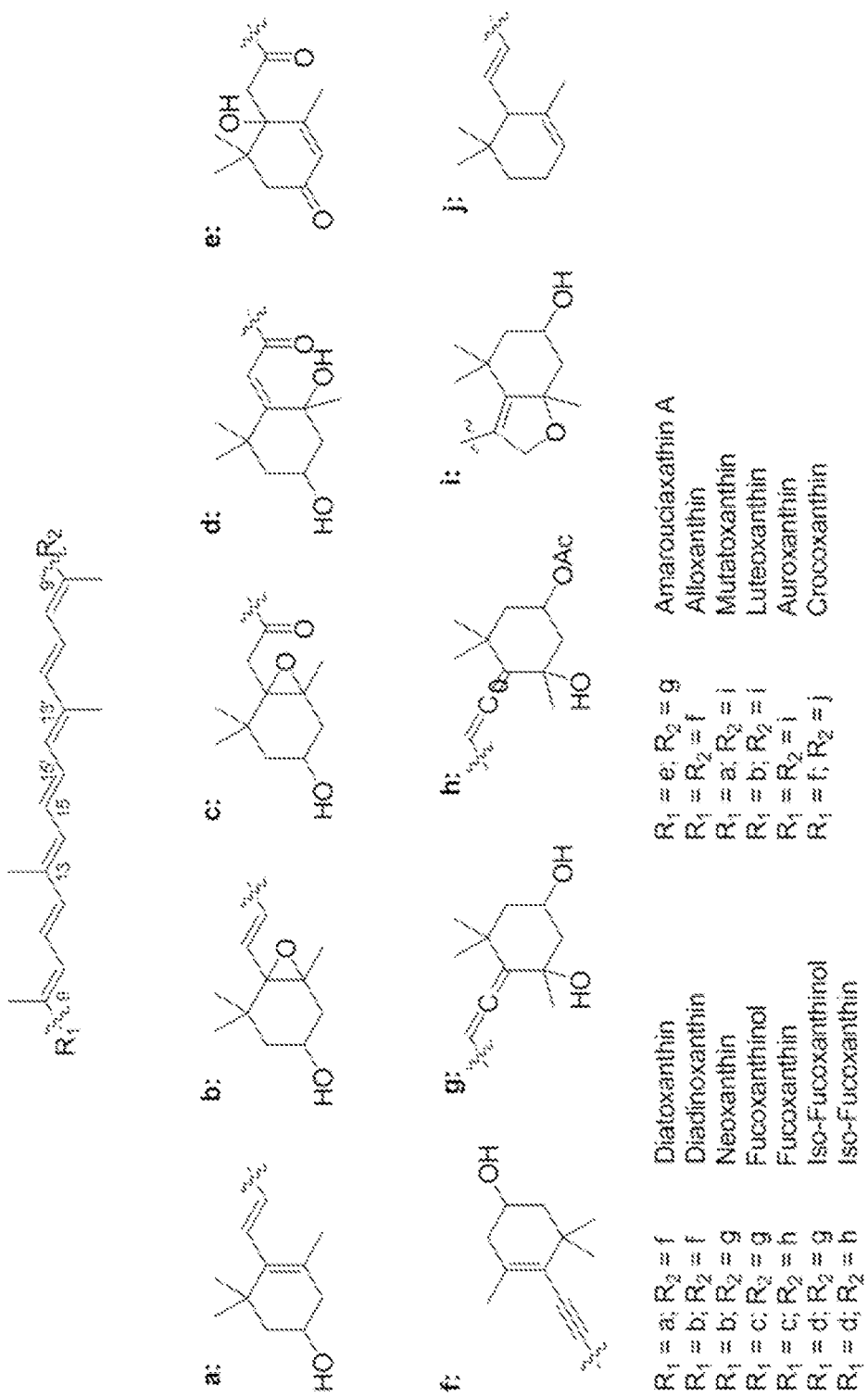
FIG. 3 shows the structure of xantophylls diatoxanthin, diadinoxanthin, neoxanthin, fucoxanthinol, fucoxanthin, iso-fucoxanthinol, iso-fucoxanthin, amarouciaxanthin A, alloxanthin, mutatoxanthin, luteoxanthin, auroxanthin and crocoxanthin.

The term "carotenoid", as used herein, refers to organic pigments which are structurally composed of a polyene hydrocarbon chain, and which may terminate in a ring. Carotenoids are divided into two classes, xanthophylls (which contain oxygen atoms) and carotenes (which contain no oxygen atoms). Examples of carotenoids suitable for use in the present invention can be found in FIGS. 1, 2 and 3.

In a particular embodiment of the invention, the carotenoid is a xanthophyll.

In a preferred embodiment, the xanthophyll is selected from the group consisting of α-cryptoxantin, β-cryptoxantin, adonirubin, adonixanthin, alloxanthin, amarouciaxanthin A, antheraxanthin, astaxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin., violaxanthin, zeaxanthin and combinations thereof.

In a particular embodiment of the invention, the carotenoid is a carotene.

In a still more preferred embodiment, the carotene is selected from the group consisting of α-carotene, β-carotene, γ-carotene, δ-carotene, ε-carotene, ζ-carotene, lycopene, neurosporene, phytoene, phytofluene and combinations thereof.

In one embodiment, the carotenes and xantophylles described above refer to the all-trans forms thereof. In other embodiment, the xantophylles and carotenes for use in the present invention include derivatives containing one or more cis double bond, including, without limitation, 9 cis derivatives, 9' cis derivatives, 13 cis derivatives, 13' cis derivatives, 15 cis derivatives, 15' cis derivatives and any combination thereof, wherein the numbering is as defined in FIGS. 1, 2 and 3. In another embodiment, the xantophylles and carotenes for use in the present invention include synthetic derivatives thereof.

The term "glucocorticoid receptor", also known as GR, GCR, or NR3C1 (nuclear receptor subfamily 3, group C, member 1), as used herein refers to the receptor to which cortisol and other glucocorticoids bind. The human, gene is shown in the Ensembl database under accession number ENSG00000113580.

As used herein, the terms "corticoids" or "corticosteroids" refer to a class of steroid hormones that are produced in the adrenal cortex of vertebrates, as well as the synthetic analogues of these hormones. Corticosteroids are involved in a wide range of physiological processes, including stress response, immune response, and regulation of inflammation, carbohydrate metabolism, protein catabolism, blood electrolyte levels, and behavior. There are two types of corticoids, glucocorticoids and mineralocorticoids.

Glucocorticoids are corticosteroids that bind to the glucocorticoid receptor. The structure of glucocorticoids comprises a steroid ring system.

As used herein, the term "cortisol" or "hydrocortisone" refers to a glucocorticoid of formula:

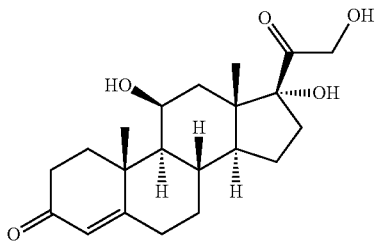

The term "treatment", as used herein, refers to any type of therapy, which is aimed at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or, at least, symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency.

In another embodiment of the invention the disease characterized by an undesired glucocorticoid activity is selected from the group consisting of cortisol-induced immunosuppression, cortisol-induced insulin resistance, altered skin barrier homeostasis, Cushing's syndrome, subclinical Cushing's syndrome, subclinical hypercortisolemia, metabolic syndrome, inflammatory bowel disease, muscle wasting and muscle dystrophy, insomnia associated to circadian rhythm disorders, hypertension, water retention, cortisol-induced DNA damage, migraine, psychosis, appetite reduction, depression, stress disorders and cognitive disorders such as Alzheimer's disease catatonia, amyotrophic lateral sclerosis, delirium, post-traumatic stress disorders, impaired memory retrieval, or borderline personality disorder.

In another embodiment, the invention relates to the carotenoid for use in the treatment or prevention of a disease mediated by glucocorticoid receptor activity wherein the disease is cancer, in which case the carotenoid is used as adjuvant in the therapy with paclitaxel or eribulin.

In an embodiment of this aspect of the invention the carotenoid is provided as an algal, fungal or plant extract.

As used herein, the term "extract" refers to a product obtained by an extractive process on any of the organisms or plants listed above, either by soaking said organisms or plants with a solvent or by extraction with more sophisticated techniques involving the use of pressure or supercritical fluids. In some cases, extracts may be subjected to a chemical saponification process in order to remove unwanted fractions from the extract.

In the context of the present invention, the term "algal" or "algae" relates to both microalgae and macroalgae. Examples of suitable microalgae for the provision of carotenoids include microalgae from the phylums Cyanophyta, Chlorophyta, Rhodophyta, Heterokontophyta, and Haptophyta. In an embodiment, the algae from the phylum Cyanophyta is Spirulina (Arthrospira), *Aphanizomenon flos-aquae, Anabaena cylindrica* or *Lyngbya majuscule*. In another embodiment, the algae from the phylum Chlorophyta is *Chlorella, Scenedesmus, Dunaliella, Tetraselmis, Haematococcus, Ulva, Codium* or *Caulerpa* spp. In another embodiment, the algae from the phylum Rhodophyta is *Porphyridium cruentum, Gracilaria* sp. *Grateloupia* sp, *Palmaria* sp. *Corallina* sp., *Chondrus* crispus, *Porphyra* sp. or *Rhodosorus* sp. In another embodiment, the algae from the phylum Heterokontophyta is *Nannochlorropsis oculata, Odontella aurita, Phaeodactylum tricornutum. Fucus* sp. *Sargassum* sp. *Padina* sp., *Undaria pinnatifida*, or *Laminaria* sp. In another embodiment, the algae from the phylum Haptophyta is *Isochrysis* sp. *Tisochrysis* sp. or *Pavlova* sp.

In another embodiment, the algae is *Chrypthecodinium cohnii, Schizochytrium, Ulkenia* or *Euglena gracilis*. In yet another embodiment, the algae is a green microalga such as *Chlorella, Scenedesmus, Dunialiella* (for beta-carotene), *Haematococcus* (for astaxanthin) and Bracteacoccus; haptophyte microalgae such as *Isochrysis* (for fucoxanthin and lutein); and heterokontophyta microalgae such as *Phaeodactylum, Ochromonas* and *Odontella*. Examples of suitable macroalgae comprise all brown algae, and in particular *Fucus vesiculosus, Fucus evanescens, Laminaria* sp., and *Sargassum* sp. (all for fucoxanthin).

Certain fungi are known to produce xantophylls, such as *Xanthophyllomyces dendrorhous*. In addition, carotenoids can also be obtained from animal sources such as egg yolk.

Plants and plant parts suitable for the production of carotenoids include, without limitation, marigold flowers, maize, kiwi, red seedless grapes, zucchini, pumpkin, spinach, orange pepper, yellow squash, cucumber, pea, green pepper, red grape, butternut, orange, honeydew, celery, green grapes, Brussels sprouts, scallions, green beans, broccoli, apple, mango, green lettuce, tomato, peach, yellow pepper, nectarine, red pepper, carrots, cantaloupe, apricots, bell peppers and green kidney beans.

In some embodiments, the extract for use according to the invention refers to a "total extract" or "crude extract", which refers to the collection of molecules originated from the cells and almost no fragments or debris of cell walls and large organelles. According to one exemplary embodiment, the total extract may be obtained by using a lysis buffer, but the present invention is not limited thereto. However, the total extract may be extracted using any extraction method known in the art.

Methods to obtain extracts are conventional and well known by the skilled person. Normally, carotenoids are brought into solution by breaking the cells containing them. There are several methods to achieve this, such as repeated freezing and thawing, sonication, homogenization by high pressure, filtration, or permeabilization by organic solvents.

In some embodiments, the extract is at least partially fractionated in order to enrich in the carotenoids, thereby obtaining a "carotenoid-enriched extract". Any suitable method known in the art can be used to obtain the carotenoid-enriched extract, such as solvent extraction, crystallization, extraction using supercritical carbon dioxide at very high process pressures are appropriately selected and combined to enable separation and purification of the carotenoid. In the case of solvent extraction, this is usually done with organic solvents such as, for example, acetone, hexane, methylene chloride, tert-butyl methyl ether or by solvent mixtures such as ethanol/hexane or acetone/hexane. The extractive effect can be varied on the basis of differences in polarity through different solvent mixing ratios. Enrichment of carotenoids and their esters to high concentration is possible by such an extraction.

The degree of enrichment in carotenoid can be determined in the enriched extract wherein an increase carotenoid amount with respect to the crude extract is indicative that the extract has been enriched in carotenoids. In a preferred embodiment, the carotenoid-enriched extract contains a content in carotenoids which is at least 5%, at least 10%, at least 20%, at least 30%, at least 40%, at least 50%, at least 60%, at least 70%, at least 80%, at least 90% or at least 100% of the contents found in the crude extract. In another embodiment, the carotenoid-enriched extract contains a carotenoid content which is at least 2-fold, 3-fold, 4-fold, 5-fold, 6-fold, 7-fold, 8-fold, 9.fold, 10-fold, 100-fold, 1000-fold, 10000-fold or more with respect to the content in the crude extract.

A Cosmetic Method for Preventing Premature-aging of Skin in a Subject which Comprises Administering a Carotenoid to Said Subject In a second aspect, the invention relates to a cosmetic method for preventing premature-aging of skin in a subject which comprises administering to a carotenoid to said subject.

In a particular embodiment of the invention, the carotenoid is a xanthophyll.

In a preferred embodiment, the xanthophyll is selected from the group consisting of α-cryptoxantin, β-cryptoxantin, adonirubin, adonixanthin, alloxanthin, amarouciaxanthin A, antheraxanthin, astaxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations thereof.

In a particular embodiment of the invention, the carotenoid is a carotene.

In a still more preferred embodiment, the carotene is selected from the group consisting of α-carotene, β-carotene, γ-carotene, δ-carotene, ε-carotene, ζ-carotene, lycopene, neurosporene, phytoene, phytofluene and combinations thereof.

In one embodiment, the carotenes and xantophylles described above refer to the all-trans forms thereof. In other embodiment, the xantophylles and carotenes for use in the present invention include derivatives containing one or more cis double bond, including, without limitation, 9 cis derivatives, 9' cis derivatives, 13 cis derivatives, 13' cis derivatives, 15 cis derivatives, 15' cis derivatives and any combination thereof, wherein the numbering is as defined in FIGS. 1, 2 and 3. In another embodiment, the xantophylles and carotenes for use in the present invention include synthetic derivatives thereof.

In an embodiment of this aspect of the invention the carotenoid is provided as an algal, fungal or plant extract.

As used herein, the term "cosmetic methods" relates to a method used to enhance the appearance of the skin in a subject. Cosmetics used in the cosmetic method of the invention include skin-care creams, lotions, powders, lipsticks, eye and facial makeup, towelettes, gels, deodorants, hand sanitizer, baby products, bath oils, bubble baths, bath salts, butters and many other types of products.

In a particular embodiment of the invention, the premature aging of skin is caused by corticoids.

All the terms and embodiments previously described are equally applicable to these aspects of the invention.

A method for Modulating an Activity of a Glucocorticoid Receptor Comprising Contacting the Receptor with a Carotenoid In a third aspect, the invention relates to a method for modulating an activity of a glucocorticoid receptor comprising contacting the receptor with a carotenoid.

In a particular embodiment of the invention, the carotenoid is a xanthophyll.

In a preferred embodiment, the xanthophyll is selected from the group consisting of α-cryptoxantin, β-cryptoxantin, adonirubin, adonixanthin, alloxanthin, amarouciaxanthin A, antheraxanthin, astaxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations thereof.

In a particular embodiment of the invention, the carotenoid is a carotene.

In a still more preferred embodiment, the carotene is selected from the group consisting of α-carotene, β-carotene, γ-carotene, δ-carotene, ε-carotene, ζ-carotene, lycopene, neurosporene, phytoene, phytofluene and combinations thereof.

In one embodiment, the carotenes and xantophylles described above refer to the all-trans forms thereof. In other embodiment, the xantophylles and carotenes for use in the present invention include derivatives containing one or more cis double bond, including, without limitation, 9 cis derivatives, 9' cis derivatives, 13 cis derivatives, 13' cis derivatives, 15 cis derivatives, 15' cis derivatives and any combination thereof, wherein the numbering is as defined in FIGS. 1, 2 and 3. In another embodiment, the xantophylles and carotenes for use in the present invention include synthetic derivatives thereof.

In an embodiment of this aspect of the invention the carotenoid is provided as an algal, fungal or plant extract.

In a particular embodiment, the carotenoid is administered to a subject at risk of or experiencing symptoms of a disease characterized by increase glucocorticoid receptor activity.

In a preferred embodiment, the carotenoid is administered as part of a food, a drink, a nutraceutical composition, pharmaceutical composition, functional food, functional nutrition product, medical food, medical nutrition product, dietary supplement or botanical drug.

In the context of the invention, a product is said to be a "food" when its use in human or animal food is safe according to the Codex Alimentarius of a country or of an organization, for example, the Food and Agriculture Organization (FAO) of the United Nations or the World Health Organization (WHO); consequently, a "food" product is a nontoxic product "suitable for use thereof in food" and therefore both expressions are synonyms and are indistinctly used in this description.

As used herein, the term "nutraceutical", derived from nutrition and pharmaceutical, refers to a product made from a food, but which may be found in pill form, powder form and/or other alternative dosage forms not usually associated with food and which has beneficial properties for the treatment and/or prevention of diseases.

As used herein, the term "pharmaceutical compositions" includes liquid, solid or semi-solid formulations. The pharmaceutical compositions will comprise suitable excipients for each formulation and will be conventionally prepared by methods known by the persons skilled in the art. The excipients will be chosen according to the selected pharmaceutical dosage form. A review of the different pharmaceutical dosage forms of drugs and of their preparation can be found in the book "Tratado de Farmacia Galénica", by C. Faulí Trillo, 10th Edition, 1993, Luzán 5, S. A. de Ediciones.

As used herein, the term "nutritional composition" of the present invention relates to a food product that beneficially affects one or more functions of the body, so as to provide better health and wellness. Accordingly, such a nutritional composition may be intended for the prevention and/or treatment of a disease or a disease causing factor. Therefore, the term "nutritional composition" of the present invention can be used as a synonym for functional food or foods for particular nutritional purposes, or medical food. A nutritional composition is similar to that of a conventional food and consumed as part of a normal diet appearance.

In a preferred embodiment of the invention, the subject is a human.

In a more preferred embodiment of the invention, the symptoms of a disease characterized by increased glucocorticoid receptor activity are selected from the group consisting of impaired cognitive functions, depression, jet-lag, stress disorders, cardiovascular disorders and osteoporosis.

All the terms and embodiments previously described are equally applicable to these aspects of the invention.

A Composition Comprising a Carotenoid and a Taxane

In a fourth aspect the invention relates to a composition comprising a carotenoid and a taxane.

The term composition (hereinafter "the composition of the invention") refers to a composition comprising at least one carotenoid and at least one taxane, as well as any other ingredient or ingredients, and any product which results, directly or indirectly, from combination, complexation, or aggregation of any two or more of the ingredients, from dissociation of one or more of the ingredients, or from other types of reactions or interactions of one or more of the ingredients.

"Taxanes", also known as "taxoids", as used herein refers to a class of diterpenes originally identified in plants of the genus *Taxus*, which are characterized by a taxadiene core (taxa-4,11-diene) and which are may bind to tubulin, promoting microtubule assembly and stabilization and/or prevent microtubule depolymerization. The taxanes comprise such molecules as paclitaxel, docetaxel, cabazitaxel, hongdoushan A, hongdoushan B and hongdoushan C, larotaxel, milataxel, tesetaxel, and/or orataxel. Compounds of this family are well known in the art for their use in the treatment of cancer due to their inhibition of microtubules' depolymerization.

Different formulations of taxanes are cited in Hennefent, K. L. & Govindan, R., 2006, Annals of Oncology, 17:735-749. The person skilled in the art will acknowledge that such formulations can also serve as basis for the compositions of the invention.

Taxanes include paclitaxel, as well as any active taxane derivative or pro-drug. In some embodiments, the taxane is an albumin-coated nanoparticle (e.g., nano-albumin bound (nab)-paclitaxel, i.e., ABRAXANE(®) and/or nab-docetaxel, ABI-008). In some embodiments, the taxane is nab-paclitaxel (ABRAXANE(®)). In some embodiments, the taxane is formulated in CREMAPHOR(®) (e.g., TAXOL (®)) and/or in Tween such as polysorbate 80 (e.g., TAXOTERE(R)). In some embodiments, the taxane is liposome-encapsulated taxane. In some embodiments, the taxane is a prodrug form and/or conjugated form of taxane (e.g., DHA covalently conjugated to paclitaxel, paclitaxel poliglumex, and/or linoleyl carbonate-paclitaxel). In some embodiments, the paclitaxel is formulated with substantially no surfactant (e.g., in the absence of CREMAPHOR and/or Tween-such as TOCOSOL(®) paclitaxel).

"Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art, or obtained from a variety of commercial sources, including for example, Sigma Chemical Co., St. Louis, Mo. (T7402 from Taxus brevifolia; or T-1912 from Taxus yannanensis). Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

The compositions of the invention may also comprise any pharmaceutically acceptable carrier. The term "carrier" or "vehicle" refers to a diluent or excipient with which the active ingredient is administered. Such pharmaceutical carriers can be sterile liquids, such as water and oils, including those of petroleum, animal, plant or synthetic origin, such as peanut oil, soybean oil, mineral oil, sesame oil and the like. Water or aqueous solutions of saline solution and aqueous dextrose and glycerol solutions, particularly for injectable solutions, are preferably used as carriers. Suitable pharmaceutical carriers are described in "Remington's Pharmaceutical Sciences" by E. W. Martin, 1995. Preferably, the carriers of the invention are approved by a regulatory agency of the Federal or a state government or listed in the United States Pharmacopoeia or another generally recognized pharmacopeia for use in animals, and more particularly in humans.

The molar concentrations of the components forming part of the composition of the invention can vary, but preferably include ratios of the two components between 50:1 and 1:50, more preferably between 20:1 and 1:20, between 1:10 and 10:1, between 5:1 and 1:5.

The compositions of the invention are formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In some embodiments, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition can also include a solubilizing agent and a local anesthetic such as lignocamne to ease pain at the site of the injection.

A Composition Comprising a Carotenoid and a Taxane for Use in the Treatment of Cancer In a fifth aspect the invention relates to a composition comprising a carotenoid and a taxane for use in the treatment of cancer As used herein, the terms "treat", "treatment" and "treating" refer to the reduction or amelioration of the progression, severity and/or duration of a proliferative disorder, or the amelioration of one or more symptoms (preferably, one or more discernible symptoms) of a disease or disorder, e.g., a proliferative disorder resulting from the administration of one or more therapies (e.g., one or more therapeutic agents such as a compound of the invention). In specific embodiments, the terms "treat", "treatment" and "treating" refer to the amelioration of at least one measurable physical parameter of a disease or disorder, e.g., a proliferative disorder, such as growth of a tumor, not necessarily discernible by the patient. In other embodiments the terms "treat", "treatment" and "treating" refer to the inhibition of the progression of a disease or disorder, e.g., a proliferative disorder, either physically by, e.g., stabilization of a discernible symptom, physiologically by, e.g., stabilization of a physical parameter, or both. In other embodiments the terms "treat", "treatment" and "treating" refer to the reduction or stabilization of tumor size or cancerous cell count.

In a preferred embodiment, the proliferative disorder is cancer. The term "cancer" refers to a group of diseases involving abnormal, uncontrolled cell growth and proliferation (neoplasia) with the potential to invade or spread (metastasize) to other tissues, organs or, in general, distant parts of the organism; metastasis is one of the hallmarks of the malignancy of cancer and cancerous tumors. The abnormal growth and/or proliferation of cancerous cells is the result of a combination of genetic and environmental factors that alter their normal physiology. The growth and/or proliferation abnormalities of cancerous cells result in physiological disorders and, in many cases, death of the individual, due to the dysfunctionality or loss of functionality of the cell types, tissues and organs affected.

The term "cancer" includes, but is not restricted to, cancer of the breast, heart, small intestine, colon, spleen, kidney, bladder, head, neck, ovaries, prostate gland, brain, pancreas, skin, bone, bone marrow, blood, thymus, womb, testicles, hepatobiliary system and liver; in addition to tumors such as, but not limited to, adenoma, angiosarcoma, astrocytoma, epithelial carcinoma, germinoma, glioblastoma, glioma, hemangioendothelioma, hemangiosarcoma, hematoma, hepatoblastoma, leukemia, lymphoma, medulloblastoma, melanoma, neuroblastoma, hepatobiliary cancer, osteosarcoma, retinoblastoma, rhabdomyosarcoma, sarcoma and teratoma. Furthermore, this term includes acrolentiginous melanoma, actinic keratosis adenocarcinoma, adenoid cystic carcinoma, adenomas, adenosarcoma, adenosquamus carcinoma, astrocytic tumors, Bartholin gland carcinoma, basal cell carcinoma, bronchial gland carcinoma, capillary carcinoid, carcinoma, carcinosarcoma, cholangiocarcinoma, cystadenoma, endodermal sinus tumor, endometrial hyperplasia, endometrial stromal sarcoma, endometrioid adenocarcinoma, ependymal sarcoma, Ewing sarcoma, focal nodular hyperplasia, germ cell tumors, glioblastoma, glucagonoma, hemangioblastoma, hemagioendothelioma, hemagioma, hepatic adenoma, hepatic adenomastosis, hepatocellular carcinoma, hepatobilliary cancer, insulinoma, intraepithelial neoplasia, squamous cell intraepithelial neoplasia, invasive squamous-cell carcinoma, large cell carcinoma, leiomyosarcoma, melanoma, malignant melonoma, malignant mesothelial tumor, medulobastoma medulloepithelioma, mucoepidermoid carcinoma, neuroblastoma, neuroepithelial adenocarcinoma, nodular melanoma, osteosarcoma, papillary serous adenocarcinoma, pituitary tumors, plasmacytoma, pseudosarcoma, pulmonary blastoma, renal cell carcinoma, retinoblastoma, rhabdomyosarcoma, sarcoma, serous carcinoma, microcytic carcinoma, soft tissue carcinoma, somatostatin secreting tumor, squamous carcinoma, squamous cell carcinoma, undifferentiated carcinoma, uveal melanoma, verrucous carcinoma, vipoma, Wilm tumor, intracerebral cancer, head and neck cancer, rectal cancer, astrocytoma, glioblastoma, microcytic cancer and non-microcytic cancer, metastatic melanoma, androgen-independent metastatic prostate cancer, androgen-dependent metastatic prostate cancer and breast cancer.

The person skilled in the art will know that several taxanes are currently approved for use as chemotherapeutic agents against different types of cancer. Paclitaxel is used against ovarian cancer, breast cancer, lung cancer, Kaposi sarcoma, cervical cancer, and pancreatic cancer. Docetaxel is used against breast cancer, head and neck cancer, stomach cancer, prostate cancer and non small-cell lung cancer. Cabazitaxel is currently approved for the treatment of hormone-refractory prostate cancer.

In a particular embodiment of the invention, the cancer to be treated with the composition comprising a carotenoid and a taxane is a breast cancer. In an even more preferred embodiment, the breast cancer is a breast carcinoma. In an even more preferred embodiment, the breast carcinoma is a breast adenocarcinoma. In an even yet more preferred embodiment, the breast adenocarcinoma is triple negative adenocarcinoma.

A Carotenoid for Use as Adjuvant in the Treatment of Cancer with a Taxane-Containing Chemotherapy In a sixth aspect, the invention relates to a carotenoid for use as an adjuvant in the treatment of cancer with a taxane-containing chemotherapy.

"Adjuvant", in the context of cancer therapy, refers to therapy against cancer that is administered besides the primary or initial therapeutic agent in order to maximize its effectiveness, reduce the probability of recurrence of the cancer and/or increase the time between applications of therapy. The use of the adjuvant is also referred to as "adjuvant therapy", "adjunct therapy", "add-on therapy" or "adjuvant care". Since the adjuvant modifies the effects of another agent, the adjuvant therapy modifies another therapy. Adjuvant therapy is used together not only with chemotherapy but also with hormone therapy, radiation therapy, targeted therapy, biological therapy and/or surgery. Adjuvant therapy can be administered after the primary therapeutic agent, concurrently, or before it (in which case it's denominated "neoadjuvant therapy").

In the context of the invention, the cancer therapy is chemotherapy, more specifically a taxane-comprising chemotherapy. Accordingly, in the context of the invention, the adjuvant therapy is a carotenoid used before, concurrently and/or after the taxane-containing chemotherapy.

In a preferred embodiment of the invention, the cancer treated with taxane containing chemotherapy that the carotenoid is an adjuvant for is breast cancer. In a more preferred embodiment of the invention, the breast cancer is a breast carcinoma. In a yet more preferred embodiment of the invention, the breast carcinoma is a breast adenocarcinoma. In an even more preferred embodiment, the breast adenocarcinoma is triple negative breast adenocarcinoma.

EXAMPLES

The invention is hereby described by way of the following examples, which are to be construed as merely illustrative and not limitative of the scope of the invention.

Example 1

Effects of Xanthophylls on Glucocorticoid Receptors

The present study aimed to determine which carotenoids act as antagonists of glucocorticoid receptors. The effects of neoxanthin, fucoxanthin, iso-fucoxanthinol and lutein (xanthophylls) and of beta-carotene (carotene) were assessed.

Materials and Methods

An antagonist assay for GR was performed. In this assay, an engineered cell line (UAS-bla HEK 293T) expressing GR is used to test the action of different carotenoids based on mammalian-optimized Beta-lactamase reporter gene (bla) combined with a FRET-enabled substrate, provides the assay with a sensitive detection method.

GR-UAS-bla HEK 293T cells contain the ligand binding domain (LBD) of the human Gluocorticoid receptor (GR) fused to the DNA-binding domain of GAL4 stably integrated in the GeneBLAzer®UAS-bla HEK 293T cell line. These cells stably express a beta-lactamase reporter gene under the transcriptional control of an upstream activator sequence (UAS). When an agonist binds to the LBD of the GAL4 (DBD)-GR (LBD) fusion protein, the protein binds to the UAS, resulting in expression of beta-lactamase.

GR-UAS-bla HEK 293T cells are thawed and resuspended in Assay Media (DMEM phenol red free, 2% CD-treated FBS, 0.1 mM NEAA, 1 mM Sodium Pyruvate, 100 U/mL/100 µg/mL Pen/Strep) to a concentration of 625,000 cells/mL. 4 µL of a 10× serial dilution of RU-486 (control antagonist starting concentration, 10 nM) or compounds are added to appropriate wells of a TC-Treated assay plate. 32 µL of cell suspension is added to the wells and pre-incubated at 37° C./5% CO2 in a humidified incubator with compounds and control antagonist titration for 30 minutes. 4 µL of 10× control agonist. Dexamethasone at the pre-determined EC80 concentration is added to wells containing the control antagonist or compounds. The plate is incubated for 16-24 hours at 37° C./5% CO2 in a humidified incubator. 8 µL of 1 µM Substrate Loading Solution is added to each well and the plate is incubated for 2 hours at room temperature. The plate is read on a fluorescence plate reader.

Results and Discussion

Figure 4:
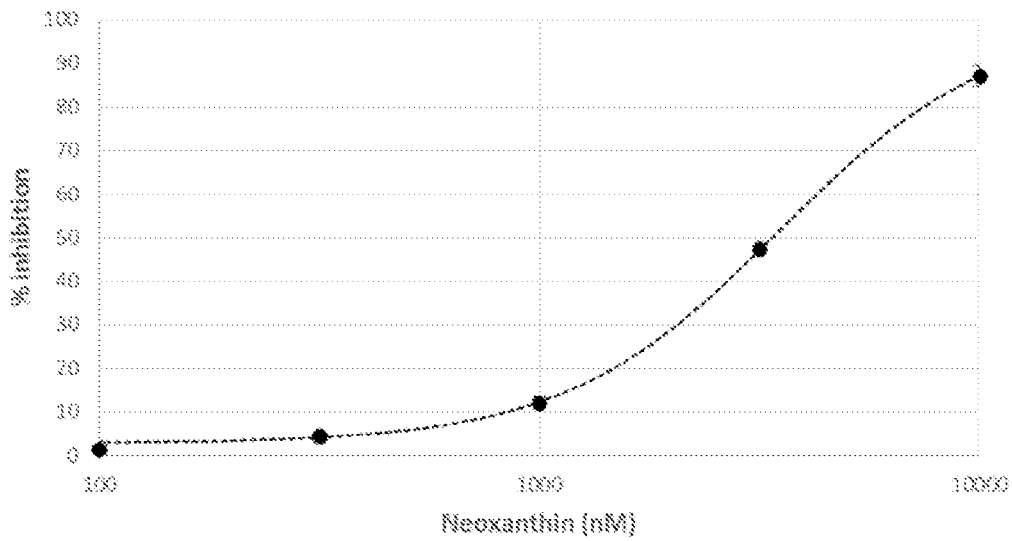
FIG. 4 shows the dose-response curve of neoxanthin action on GR. Dexamethasone was used as glucocorticoid stimuli. Mifepristone was the control antagonist of the assay (IC50 2.46 nM). Error bars indicate standard deviation.

The putative antagonist effect of carotenoids on GR was evaluated in different assays. Firstly, neoxanthin was tested against the agonist dexamethasone (FIG. 4). Neoxanthin inhibitory action starts between 0.1 and 0.3 µM and is above 85% at 10 µM.

Figure 5:
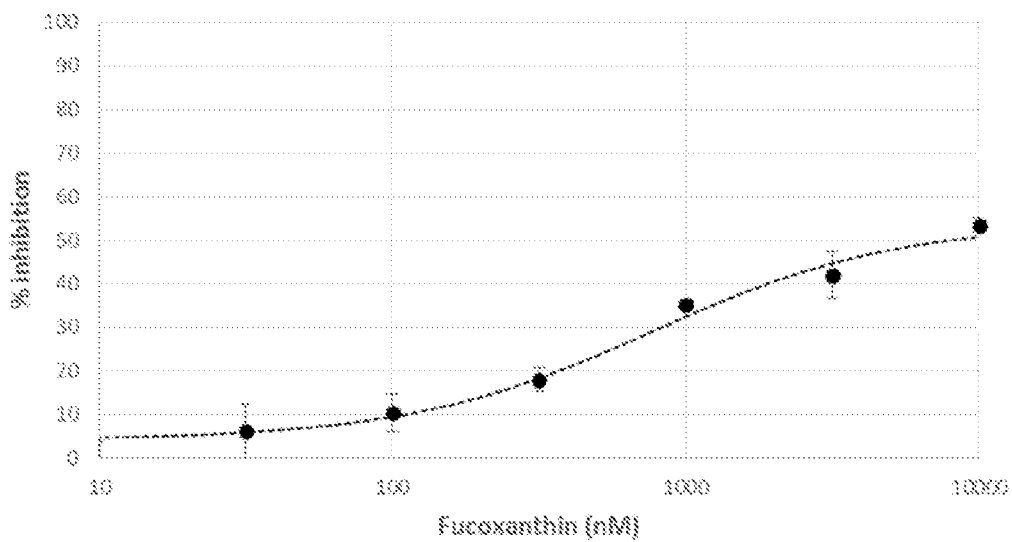
FIG. 5 shows the dose-response curve of fucoxanthin action on GR. Dexamethasone was used as glucocorticoid stimuli. Mifepristone was the control antagonist of the assay (IC50 1.05 nM). Error bars indicate standard deviation.

On a second assay, fucoxanthin activity was analyzed. The data obtained was modelled to a sigmoidal dose response curve shown in FIG. 5. In this case, fucoxanthin acts as an antagonist from a concentration of 30 nM but only achieves 50% of inhibition at 10 µM. It is clear that both compounds exercise an antagonist effect on GR: neoxanthin acts as a total antagonist, while fucoxanthin acts as a parcial antagonist.

Figure 6:
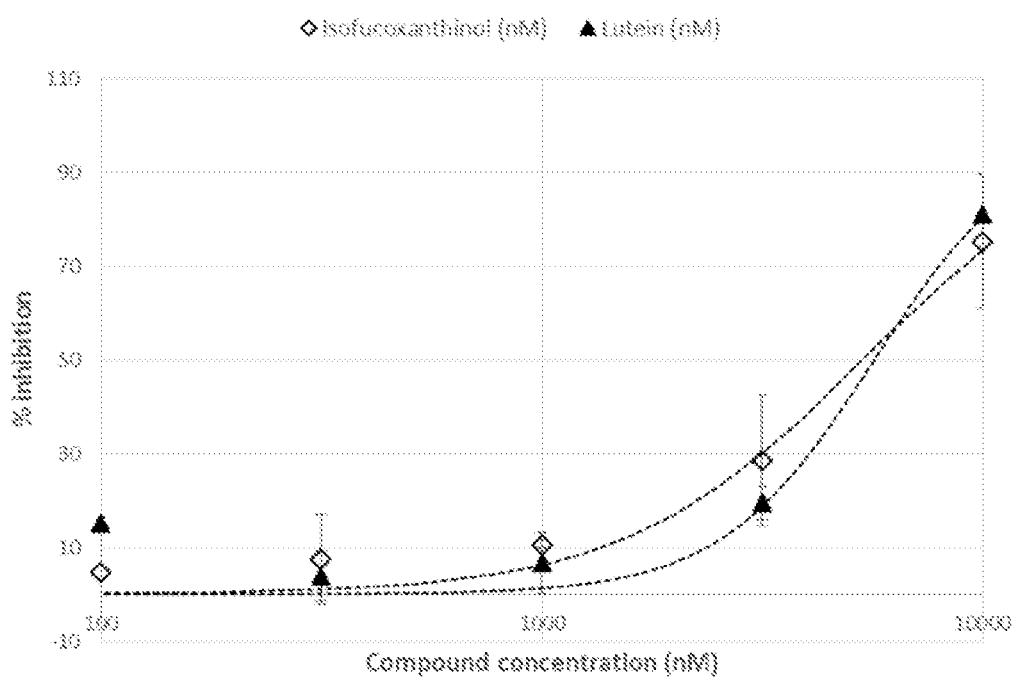
FIG. 6 shows the dose-response curve of different xanthopylls' antagonism to GR. Dexamethasone was used as glucocorticoid stimuli. Mifepristone was the control antagonist of the assay (IC50 0.84 nM).

Similar results were obtained when iso-fucoxanthinol and lutein were analyzed (FIG. 6). They both achieve a maximum of 80% GR inhibition when used at 10 mM.

Figure 8:
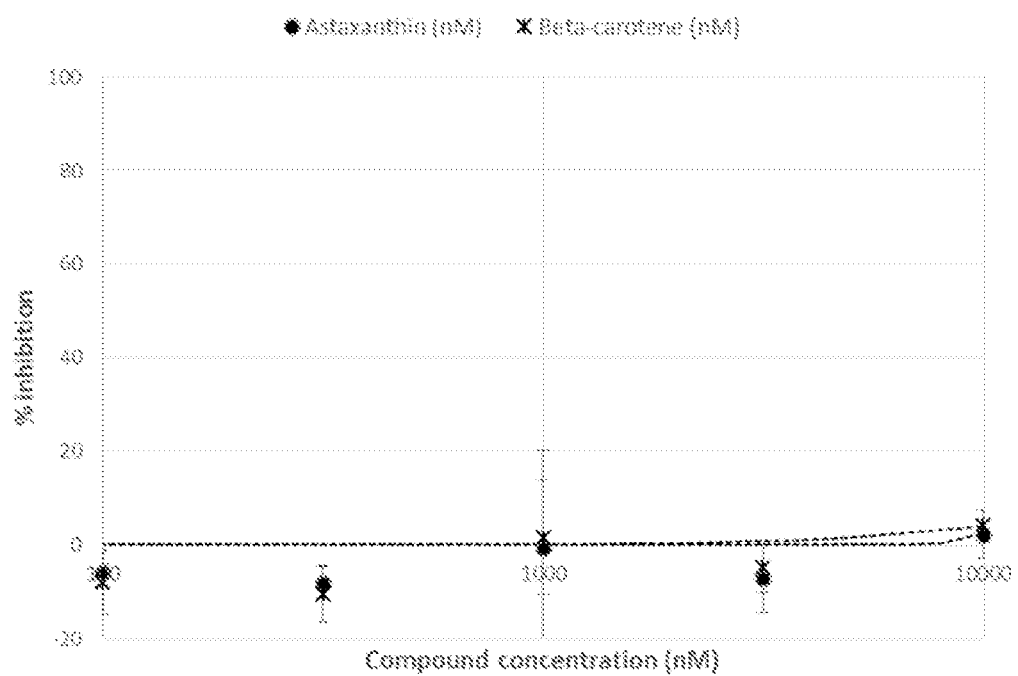
FIG. 8: shows the dose-response curve of astaxanthin and beta-carotene antagonism to GR. Dexamethasone was used as a glucocorticoid stimuli. Mifepristone was the control antagonist of the assay (IC50 0.84 nM). Error bars indicate standard deviation.

Astaxanthin was tested against the agonist dexamethasone. On a different assay, beta-carotene activity was analyzed. The data obtained is modelled to a sigmoidal dose response curve shown in FIG. 8. It is clear that neither compounds exercise an antagonist effect on GR, as they are not capable of significantly inhibiting dexamethasone action. This results contrast with the results obtained with other carotenoids.

In conclusion, certain xanthophylls (neoxanthin, fucoxanthin, iso-fucoxanthinol and lutein) are able to inhibit or modulate the action of glucocorticoid agonists. However, other xantophylls (astaxanthin) and beta-carotene (a carotene) are not capable of significantly antagonizing dexamethasone action on the receptor.

Example 2

Effects of Xanthophylls on Progesterone Receptors

After studying the effect of neoxanthin and fucoxanthin on GR and prove they are glucocorticoid antagonists, the question of whether they also affect progesterone receptors (PR) was raised. Some well-known GR antagonists, such as mifepristone, have different effects among the estrogen receptor family.

The present study aimed to determine if neoxanthin and fucoxanthin act as antagonists of progesterone receptors.

Materials and Methods

An antagonist assay for PR was performed. In this assay, an engineered cell line (UAS-bla HEK 293T) expressing PR is used to test the action of two xanthophylls. The detection method consists in GeneBLAzer® technology, based on mammalian-optimized Beta-lactamase reporter gene (bla) combined with a FRET-enabled substrate.

Results and Discussion

Figure 7:
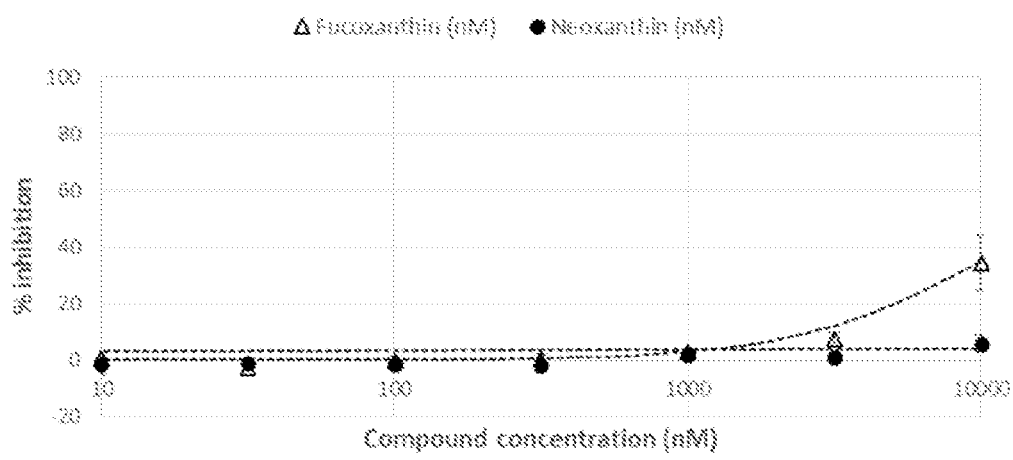
FIG. 7 shows the dose-response curve of neoxanthin and fucoxanthin action on PR. R5020 compound was used as progesterone stimuli. Mifepristone was the control antagonist of the assay (IC50 1.71 nM). Error bars indicate standard deviation.

In FIG. 7, neoxanthin and fucoxanthin were tested against the agonist promegestone (R5020). None of them showed an important antagonist action, although fucoxanthin achieved 30% of inhibition at the highest concentration tested.

In conclusion, these xanthophylls are able to block glucocorticoid effects without showing side-effects on progesterone receptors.

Example 3

Neoxanthin and Fucoxanthin Protect DNA from Cortisol-induced Damage

The object of this study was to determine the protective effect of neoxanthin and fucoxanthin in front of DNA damage induced by cortisol.

Materials and Methods

Cell Culture

HaCat cell line, a spontaneously transformed aneuploid immortal keratinocyte cell line from adult human skin was used. Keratinocytes were cultured in DMEM medium supplemented with 10% FCS. Culture was incubated at 37° C. with 5% CO2 and 90% humidity. Assays were performed with cells between 80% and 90% of confluence and with a cell viability above 90% (tested by trypan blue staining).

DNA Damage Assay 20000 cells per experimental condition were seeded in 24 well plates with 1 mL of medium for 24 h. Culture medium was substituted for not supplemented DMEM and after a 24 hour incubation, compounds were added at 0.1 µM to assay wells. Cell culture was kept in these conditions for 1 h at 37° C. before the addition of 10 µM hydrocortisone to assay wells and control. 5 mM of hydrogen peroxide was used as a positive control. Plate was incubated for 30 min before the DNA extraction.

DNA Damage Quantification

DNA damage was quantified using the HCS DNA Damage kit (ThermoFisher®). "The HCS DNA Damage kit simultaneously and quantitatively measures two important cell-health parameters: DNA damage and cytotoxicity. DNA damage is detected using an antibody against phosphorylated H2AX (Ser139) which is induced in response to double-strand break (DSB) formation". Plate was read using Fluoroscan at 355-460 nm for Hoechst (cell number) and 485-538 nm for the secondary antibody (DNA damage). Background is subtracted and relativized with values obtained from Hoechst staining in order to obtain the value of DNA damage relative to the cell count of each well. Results were normalized using the basal values.

Results and Discussion

Figure 9:
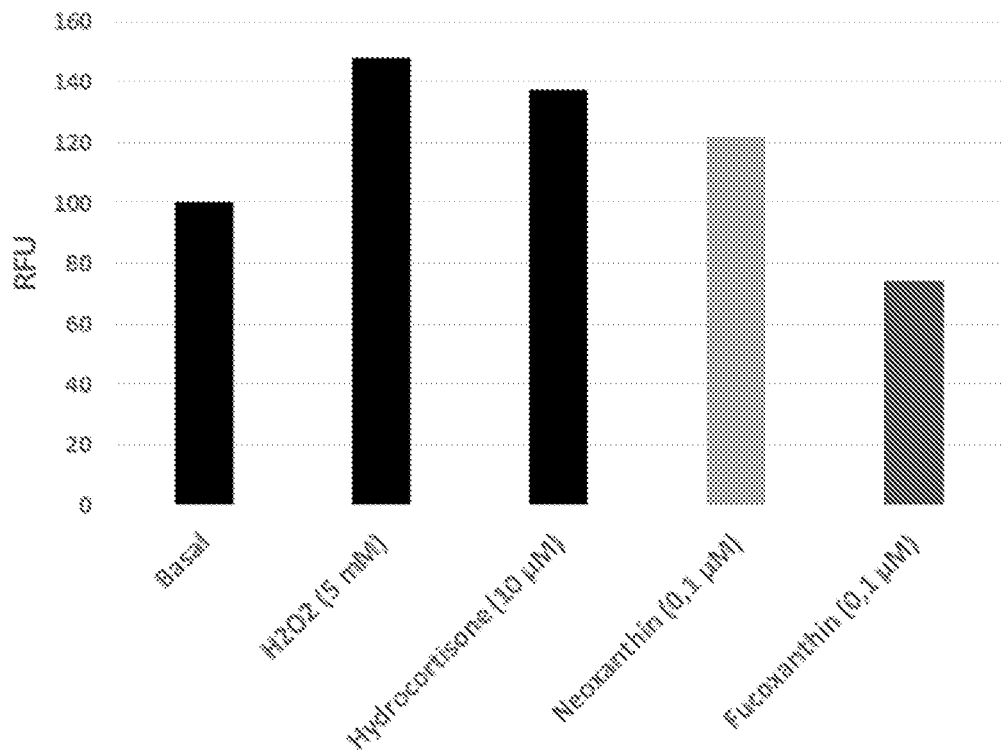
FIG. 9 shows the protective effects of neoxanthin and fucoxanthin from hydrocortisone-induced DNA damage. Data is shown in Relative Fluorescence Units (RFU).

Cortisol induces DNA damage via the induction of DSB in DNA. This can be measured using phosphorylated histone H2AX, which is induced in response to DSB (Flint et al., Psychoneuroendocrinology. 2007; 32(5):470-9 and Flint et al., Stress. 2013 January; 16(1): 114-121). DNA damage caused by hydrocortisone is about 1.5 times higher than the basal state under the assay conditions (FIG. 9). Neoxanthin and fucoxanthin proved to be capable of protecting DNA in the presence of the damage stimuli (hydrocortisone).

In conclusion, neoxanthin and fuxcoxanthin are able to protect cells from the DNA damage caused by glucocorticoid stimuli.

Example 4

Neoxanthin and Fucoxanthin Protect from Cortisol-induced p53 Down-regulation The object of this study was to determine the protective effect of neoxanthin and fucoxanthin in front of the drop in p53 production caused by cortisol.

Materials and Methods

Cell Culture

HaCat keratinocytes were cultured in DMEM medium supplemented with 10% FCS. Culture was incubated at 37C with 5% CO2 and 90% humidity. Assays were performed with cells between 80% and 90% of confluence and with a cell viability above 90% (tested by trypan blue staining).

Cell Culture for P53 Determination 20000 cells per experimental condition were seeded in 24 well plates with 1 mL of medium for 24h. Culture medium was substituted for not supplemented DMEM and after a 24 hour incubation, compounds were added at 0.1 and 1 µM to assay wells. After 1 h incubation, hydrocortisone was added at 10 µM and cells were kept under these conditions for 2 h.

P53 Quantification

P53 levels were determined using "Human Total p53 DuoSet IC ELISA" from R&D Systems. Cells were lysed in 100 µL of lysis buffer and 5 µg of total cell extract were used for the quantitative ELISA. Optical density was measured at 450 nm and background was subtracted. P53 was quantified using a standard curve and values were normalized using the basal results.

Results and Discussion

Figure 10:
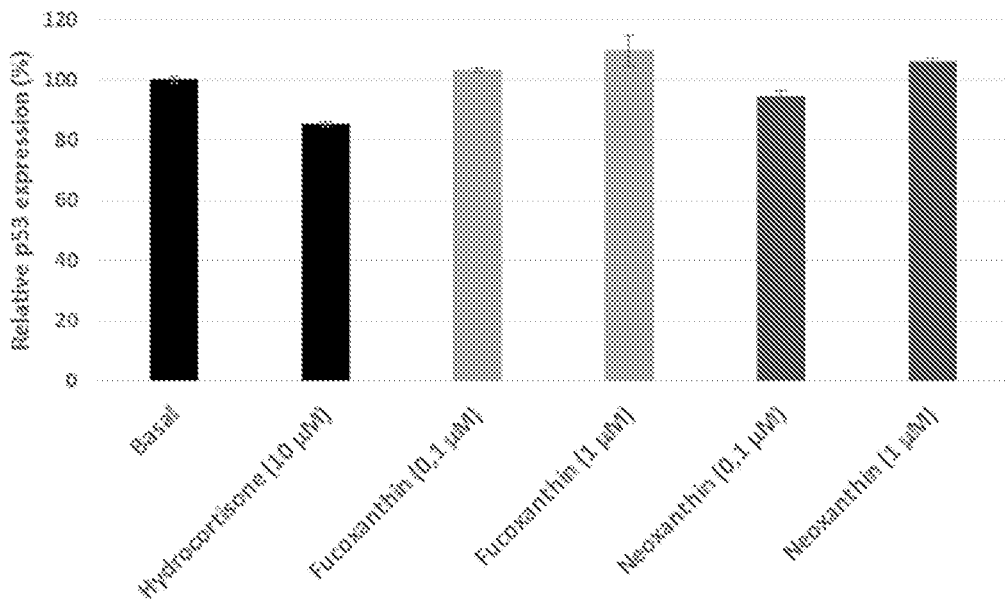
FIG. 10 shows the protective effects of fucoxanthin and neoxanthin from hydrocortisone down-regulation of p53. Data is shown as the percentage of p53 expression relative to the basal state.

Hydrocortisone causes the down-regulation of p53. As shown in FIG. 10, both fucoxanthin and neoxanthin proved to increase p53 expression in the presence of hydrocortisone.

In conclusion, neoxanthin and fucoxanthin are able to protect cells from the down-regulation of p53 caused by glucocorticoid stimuli.

Example 5

Fucoxanthin as Adjuvant in Placlitaxel-treated Triple Negative Breast Adenocarcinoma The present study aimed to determine if glucocorticoid receptor-modulating carotenoids can act as adjuvants in the treatment of cancer. For that purpose the cytotoxic effects (EC50) of fucoxanthin (063-06691, Wako Chemicals) alone and combined with paclitaxel (T1912, Sigma-Aldrich) on the triple negative breast adenocarcinoma cell line MDA-MB-231 (ECACC: 92020424) were assessed.

In a first setup, MDA-MB-231 cells were seeded in 96 well plates with 100 µL of DMEM +10% FBS and incubated at 37° C., 5% $CO_2$ and 90% humidity. After 24 hours, with a confluence and viability of between 80 and 90% as assessed by trypan blue test, cells were treated with serial dilutions (1:3) in DMEM+10% FBS of fucoxanthin solubilized in DMSO ranging from 100 µM to 15.2 nM. After 72 h, effect of the treatment was assessed by the MTT method yielding a fucoxanthin$_{EC50}$=7.46 µM.

Figure 11:
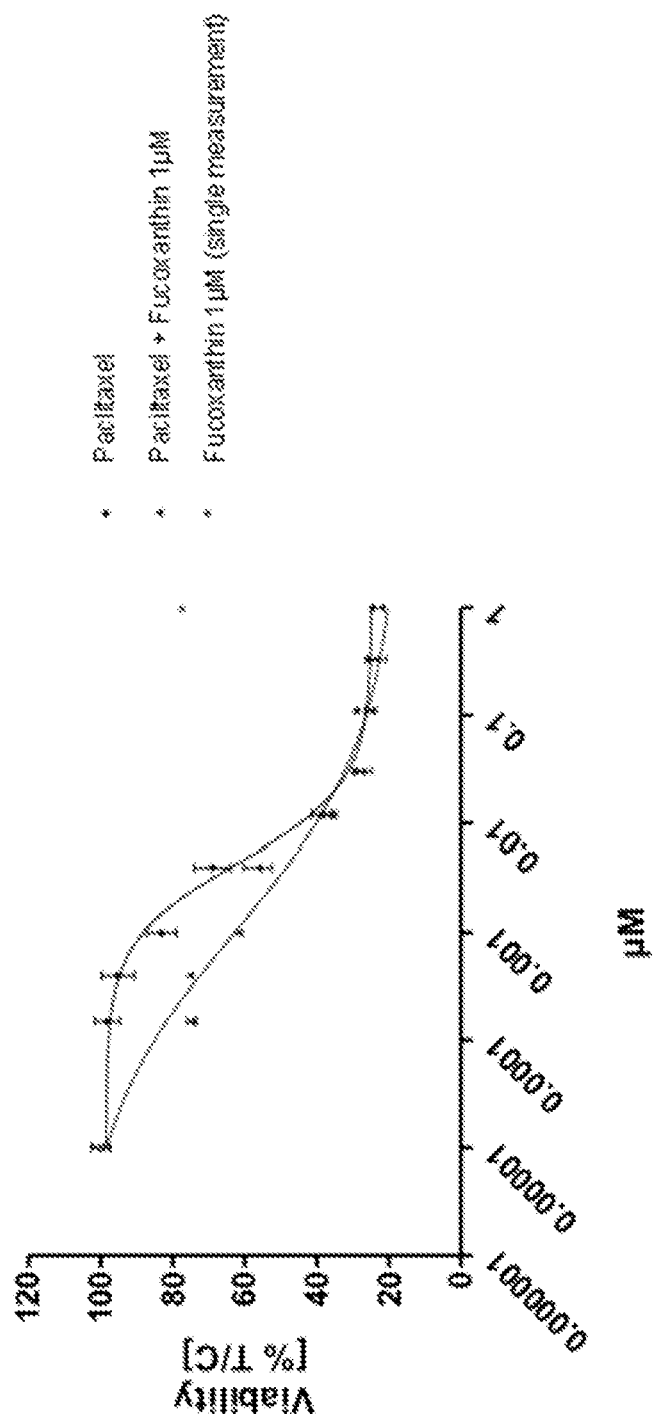
FIG. 11 corresponds to the adjuvant effects of fucoxanthin and shows a dose-response curve of paclitaxel when administered separately or together with a fixed concentration of fucoxanthin. Data is shown as cell viability in percentage.

In a second setup, MDA-MB-231 cells were seeded in 96 well plates with 100 µL of DMEM +10% FBS and incubated at 37° C., 5% $CO_2$ and 90% humidity. After 24 hours, with a confluence and viability of between 80 and 90% as assessed by trypan blue test, cells were treated with serial dilutions (1:3) of paclitaxel in DMEM+10% FBS ranging from 1 µM to 0.15 nM or with both the same concentrations of paclitaxel plus a fixed subtoxic concentration of fucoxanthin (1 µM) solubilized in DMSO (100 µM). After 72 h, effect of the treatments was assessed by the MTT method (FIG. 11).

Results of the study yielded a paclitaxel$_{EC50}$=4.4 nM, while the combination with fucoxanthin decreased EC50 to 1 nM, more than four times less than with paclitaxel alone.

The invention claimed is:

1. A method for treating a disease mediated by glucocorticoid receptor activity in a subject, which comprises administering to the subject a carotenoid which is the xanthophyll amarouciaxanthin A, and wherein the treating is by antagonizing the glucocorticoid receptor, and wherein the disease mediated by glucocorticoid receptor activity is selected from the group consisting of metabolic syndrome, Cushing's syndrome, Alzheimer's disease, and amyotrophic lateral sclerosis.

2. The method of claim 1, wherein the carotenoid is provided as an algal, fungal or plant extract.

3. The method of claim 1, wherein the subject is a human.

4. The method of claim 1, wherein the disease mediated by glucocorticoid receptor activity is metabolic syndrome.

5. The method of claim 3, wherein the disease mediated by glucocorticoid receptor activity is metabolic syndrome.

* * * * *